United States Patent
Proksa et al.

(10) Patent No.: US 9,597,042 B2
(45) Date of Patent: Mar. 21, 2017

(54) PERFUSION IMAGING

(75) Inventors: Roland Proksa, Neu Wolmstorf (DE); Michael Grass, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1231 days.

(21) Appl. No.: 13/266,556

(22) PCT Filed: Apr. 9, 2010

(86) PCT No.: PCT/IB2010/051541
§ 371 (c)(1),
(2), (4) Date: Oct. 27, 2011

(87) PCT Pub. No.: WO2010/131130
PCT Pub. Date: Nov. 18, 2010

(65) Prior Publication Data
US 2012/0045109 A1    Feb. 23, 2012

Related U.S. Application Data

(60) Provisional application No. 61/177,348, filed on May 12, 2009, provisional application No. 61/221,113, filed on Jun. 29, 2009.

(51) Int. Cl.
*G06K 9/00* (2006.01)
*A61B 6/03* (2006.01)
*A61B 6/00* (2006.01)

(52) U.S. Cl.
CPC .............. *A61B 6/032* (2013.01); *A61B 6/481* (2013.01); *A61B 6/482* (2013.01); *A61B 6/504* (2013.01); *A61B 6/507* (2013.01); *A61B 6/486* (2013.01)

(58) Field of Classification Search
None
See application file for complete search history.

(56) References Cited

U.S. PATENT DOCUMENTS

| | | | |
|---|---|---|---|
| 2007/0189443 A1* | 8/2007 | Walter et al. | 378/4 |
| 2008/0279328 A1* | 11/2008 | Zeitler et al. | 378/4 |
| 2009/0052621 A1* | 2/2009 | Walter et al. | 378/53 |

FOREIGN PATENT DOCUMENTS

| | | |
|---|---|---|
| JP | 2007175194 A | 7/2007 |
| JP | 2008142435 A | 6/2008 |

OTHER PUBLICATIONS

Heismann, B. J., et al.; Atomic number measurement precision of spectral decomposition methods for CT; 2005; IEEE Nuclear Science Symposium Conference Record; 5:2741-2742.

* cited by examiner

*Primary Examiner* — Weiwen Yang

(57) ABSTRACT

A method is disclosed that includes decomposing, with a decomposer, agent-based time series projection data for an object or a subject into at least an agent based component. A projection data decomposer includes a time series decomposer that determines agent-based projection data based on agent-based time series projection data based on at least two energy dependent components. A computer readable storage medium containing instructions which, when executed by a computer, cause the computer to perform the act of determining an agent-based component of agent-based time series projection data utilizing at least two components of the agent-based time series projection is provided.

15 Claims, 2 Drawing Sheets

PERFUSION IMAGING

CROSS REFERENCE TO RELATED APPLICATIONS

Figure 1:
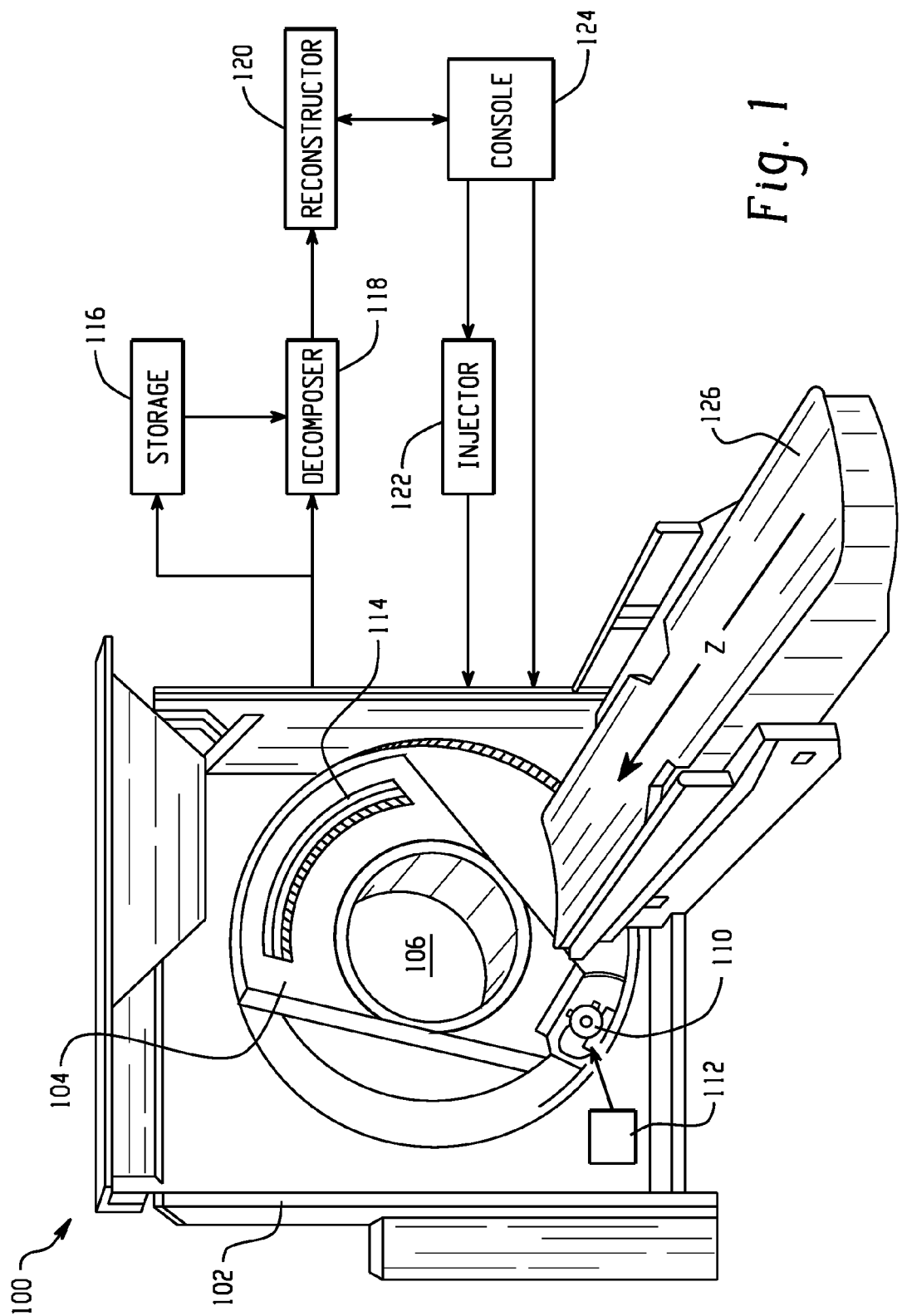

This application claims the benefit of U.S. Provisional Application Ser. No. 61/177,348 filed May 12, 2009 and U.S. Provisional Application Ser. No. 61/221,113 filed Jun. 29, 2009, both of which are incorporated herein by reference.

The following generally relates to perfusion imaging, and finds particular application to computed tomography perfusion (CTP). However, it is also amenable to other medical imaging applications and to non-medical imaging applications.

Computed tomography perfusion (CTP) imaging provides information that can be used to facilitate diagnosing patients with mal-perfusion of the brain like stroke patients. By way of example, time series images generated from such a scan can be used to identify ischemic tissue and/or differentiate between irreversibly damaged tissue (necrotic tissue or the core of the infarct) and potentially reversibly damaged tissue (at-risk tissue or the penumbra of the infarct), for example, in stroke patients.

A typical CTP procedure includes injecting a contrast agent and then several seconds after injection the patient is scanned over a predetermined time interval, and a time series of images is generated for a region of interest from the acquired data. Perfusion parameters are extracted from the time series of images. For this approach, it is assumed that the contrast material concentration depends linearly on the contrast enhancement in the images, i.e. on the increase of the CT number over a baseline.

For the calculation of regional quantitative parameters like regional cerebral blood flow (rCBF) and cerebral blood volume (rCBV), the regional contrast enhancement is compared with the contrast enhancement in a reference region (e.g., the supplying artery). Unfortunately, this can lead to erroneous results since the reconstructed images are distorted by beam hardening artifacts; for image reconstruction in conventional CT scanners, a simplified assumption is made that a mono-energetic X-ray source is used for imaging, which is not the case for clinical CT scanner, and this simplification can lead to beam-hardening artifacts.

Beam hardening artifacts can make a region of homogeneous tissue in the image appear inhomogeneous, especially if a substantial amount of bone is located around that region. The contrast enhancement is also affected by beam hardening artifact. For example, beam hardening artifact can cause the contrast enhancement to appear inhomogeneous in a region in which the contrast material concentration is constant.

Aspects of the present application address the above-referenced matters and others.

According to one aspect, a method includes decomposing, with a decomposer, agent-based time series projection data for an object or a subject into at least an agent based component.

According to another aspect, a projection data decomposer includes a time series decomposer that determines agent-based projection data based on agent-based time series projection data based on at least two energy dependent components.

According to another aspect, a computer readable storage medium containing instructions which, when executed by a computer, cause the computer to perform the steps of: determining an agent-based component of agent-based time series projection data utilizing at least two components of the agent-based time series projection.

The invention may take form in various components and arrangements of components, and in various steps and arrangements of steps. The drawings are only for purposes of illustrating the preferred embodiments and are not to be construed as limiting the invention.

Figure 2:
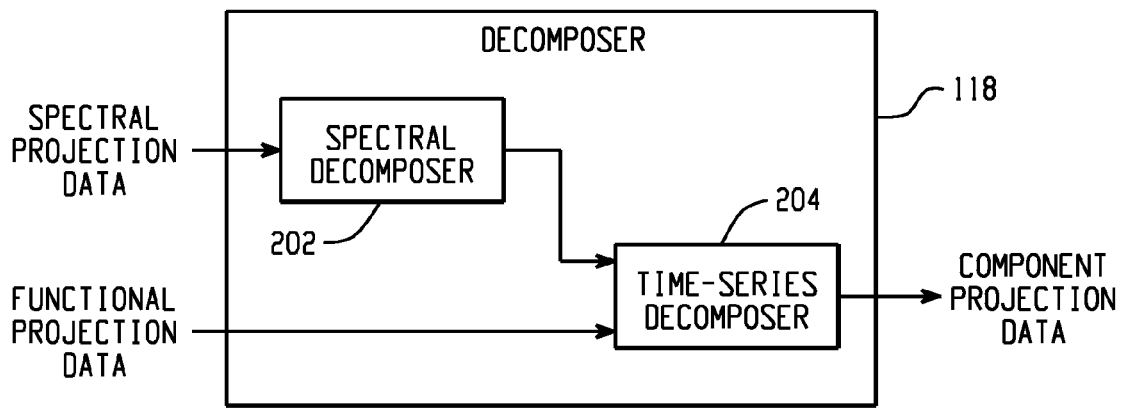
Figure 3:
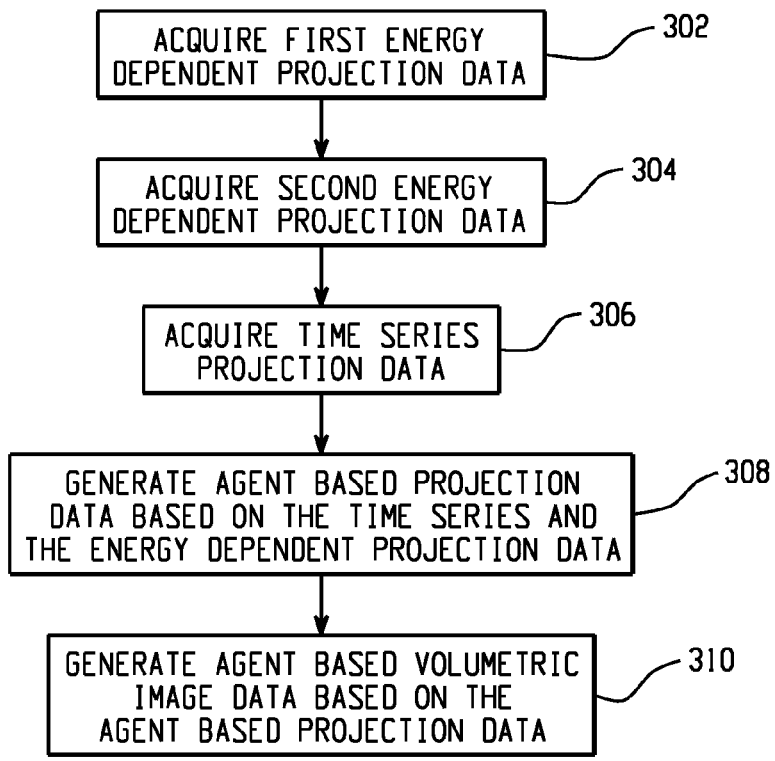

FIG. 1 illustrates an example imaging system.
FIG. 2 illustrates an example projection data decomposer.
FIG. 3 illustrates an example method.

FIG. 1 illustrates a computed tomography (CT) scanner 100 that includes a stationary gantry 102 and a rotating gantry 104, which is rotatably supported by the stationary gantry 102. The rotating gantry 104 rotates around an examination region 106 about a longitudinal or z-axis.

A radiation source 110, such as an x-ray tube, is supported by and rotates with the rotating gantry 104 around the examination region 106. The radiation source 110 emits radiation, and a collimator collimates the emitted radiation and produces a generally fan, wedge, or cone shaped radiation beam that traverses the examination region 106.

A radiation source controller 112 controls the mean emission voltage of the radiation source 110. In the illustrated embodiment, the radiation source voltage controller 112 can switch the emission voltage between at least two different voltages. This allows the system 100 to be used for multi-energy acquisitions in which the radiation source 110 generates a first radiation beam with a first energy spectrum for a first scan and an nth radiation beam with an nth different energy spectrum for an nth second scan.

A radiation sensitive detector array 114 is also supported by the rotating gantry 104 and subtends an arc across from the radiation source 110, opposite the examination region 106. The detector array 114 detects radiation that traverses the examination region 106 and generates projection data indicative thereof. The projection data can be stored in storage 116.

A processor or projection data decomposer 118 decomposes the projection data into different energy-dependent components. As described in greater detail below, in one instance the decomposer 118 decomposes the projection data into at least two components, such as photo-electric and Compton components, and, for agent-based imaging procedures, the decomposer 118 can decompose the projection data into photo-electric, Compton, and administered agent components.

A reconstructor 120 reconstructs one or more of the decomposed energy-dependent components (photo-electric, Compton and/or administered agent) and/or a combination thereof, and generates volumetric image data indicative of the examination region 106, including a region of interest of the object or subject therein. This allows for generating agent-based volumetric image data (e.g., image data without anatomical background), which can be used to generate a quantitative map for the agent for a time series of images. Beam hardening artifact may also be reduced or mitigated since the energy dependence is known.

An injector 122 is configured to administer one or more substances or agents (e.g., contrast agents, etc.) to the object or subject for a scan. The substance may alternatively be manually administered by a clinician.

A general purpose computing system 124 serves as an operator console. Software resident on the console 124 allows the operator to control the operation of the system 100, including selecting an agent-based scan protocol that includes two or more non-agent based different energy acquisitions and one or more agent based time series or perfusion acquisitions.

A patient support 126, such as a couch, supports the patient for the scan.

FIG. 2 illustrates an example projection data decomposer 118.

A first or spectral decomposer 202 spectrally decomposes projection data from the detector array 114. In the illustrated embodiment, the spectral decomposer 202 spectrally decomposes projection data acquired via at least two different scans or acquisitions performed with two different emission voltages. The spectral decomposer 202 concurrently decomposes the energy-dependent projection data into photo-electric and Compton components.

In one instance, the spectral decomposer 202 spectrally decomposes the projection data based on Equation 1:

$$M_{kVp} = \int dES(E) R_{kVp}(E) e^{-(A^1(E) + A^2(E))}.$$ Equation 1 where $M_{kVp}$ represents the energy-dependent intensity measurement, $R_{kVp}$ represents the emission spectrum, $A_1$ represents the line integrals for the photo-electric effect ($A_1 = E^{-3} \int a_1(\vec{x}) ds$), and $A_2$ represents the line integrals for the Compton effect ($A_2 = f_{KN}(E) \int a_2(\vec{x}) ds$). At least two energy-dependent intensity measurements ($M_{kVp1}$ and $M_{kVp2}$) are used to determine $A_1$ and $A_2$.

A second or time series decomposer 204 decomposes agent-based time series projection data utilizing the energy-dependent components from the above described spectral decomposition of the non-agent based projection data. By way of example, the time series decomposer 204 can decompose agent-based time series projection data, for any moment in time of the time series based on $A_1$ and $A_2$ to determine an agent based component at that moment in time.

In one instance, the time series decomposer 204 decomposes the agent based time series projection data to determine an agent-based component based on Equation 2:

$$M_{kVp}(t_i) = \int dES(E) R_{kVp}(E) e^{-(A_1(E) + A_2(e))} e^{-CA(t_i) f_{CA}(E)}$$ Equation 2 where $M_{kVp}(t_i)$ represents the energy dependent intensity measurement at time $t_i$ of the time series, $CA(t_i)$ represents the line integral of the agent at time $t_i$, and $f_{CA}(E)$ represents the energy dependent absorption of the agent. $A_1$ and $A_2$ respectively represent the line integrals for the photo-electric effect and the Compton effect as described above.

The time series decomposer 204 determines $CA(t_i)$ from EQUATION 2 using $A_1$ and $A_2$, which are determined from EQUATION 1. In one instance, $A_1$ and $A_2$ are first determined and then used to determine $CA(t_i)$. In another instance, $A_1$, $A_2$ and $CA(t_i)$ are concurrently determined. The emission voltage of the time series acquisition can be the same as one of the spectral acquisitions or different.

FIG. 3 illustrates a method for generating agent-based projection data from agent-based time series projection data.

At 302, a first non-agent based scan of a region of interest of an object or subject is performed using a first emission voltage. At 304, a second non-agent based scan of the region of interest is performed using a second different emission voltage. Both of the above scans are performed prior to administration of the agent and can be considered as baseline scans.

By way of non-limiting example, one of the scans is performed with an emission voltage in a range of about 120-160 kilo-Volts (kV) such as about 140 kV and the other scan is performed with an emission voltage in a range of about 60-100 kilo-Volts (kV) such as about 80 kV. The above ranges are provided for illustrative purposes and are not limiting.

At 306, a time series agent based perfusion scan is performed. This may include administering an agent such as a contrast agent to a patient and then after a predetermined delay continuously scanning the region of interest of the object or subject for a predetermined period of time.

At 308, agent based projection data such as an agent based component is determined for the time series projection data based on the projection data from the two non-agent based scans. The agent based projection data can be determined based on EQUATIONS 1 and 2 as described in greater detail above, or otherwise.

At 310, agent based volumetric image data is generated from the agent based projection data. The agent based volumetric image data provide quantitative agent data for the time series scan.

In one instance, the agent based volumetric image data is used to generate agent based images for the time series scan. Such images can be presented via a display of the console 124 or other computing device, or film. The agent based images emphasize contrast enhanced tissue, while de-emphasizing or visually suppressing non-contrast enhanced tissue. As noted above, such images can be used to generate a quantitative map for the agent for the time series, and various parameters such as cerebral blood flow (CBF) and cerebral blood volume (CBV), etc. can be determined therefrom.

The above may be implemented by way of computer readable instructions, which, when executed by a computer processor(s), causes the processor(s) to carry out the acts described herein. In such a case, the instructions are stored in a computer readable storage medium such as memory associated with and/or otherwise accessible to the relevant computer.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:
   determining at least two energy-dependent components based on projection data from at least two non-agent based spectral scans, wherein a first of the at least two spectral scans is performed at a first emission voltage and a second of the at least two spectral scans is performed at a second emission voltage, wherein the first and second emission voltages are different; and
   decomposing, with a decomposer, agent-based time series projection data for an object or a subject into at least an agent-based component based on the at least two energy-dependent components.

2. The method of claim 1, further comprising reconstructing the agent based component to generate agent based volumetric image data indicative of the object or the subject.

3. The method of claim 2, wherein the agent based volumetric image data provides quantitative agent data for the agent-based time series projection data.

4. The method of claim 1, wherein the at least two energy-dependent components include a photo-electric component and a Compton component.

5. The method of claim 1, further comprising determining the at least two energy-dependent components and subsequently determining the agent based component based on the at least two energy-dependent components.

6. The method of claim 1, further comprising concurrently determining the at least two energy-dependent components and the agent based component.

7. A projection data decomposer, comprising:
a microprocessor that determines at least two energy dependent components from non-contrast agent projection data generated from at least two non-contrast enhanced acquisitions performed with two different emission voltages and that determines contrast agent projection data based on contrast-enhanced projection data from a perfusion scan and the at least two energy dependent components.

8. The projection data decomposer of claim 7, wherein the at least two energy dependent components include a photo-electric component and a Compton component.

9. The projection data decomposer of claim 7, wherein the contrast agent projection data is reconstructed to generate contrast agent-based volumetric image data.

10. The projection data decomposer of claim 9, wherein the contrast agent-based volumetric image data provides a quantitative contrast agent map.

11. A non-transitory computer readable storage medium containing instructions which, when executed by a computer, cause the computer to perform the acts of:
determining at least two energy dependent components based on non-agent based projection data generated from at least two data acquisitions performed with two different emission voltages; and
determining an agent-based component based on agent-based time series projection data utilizing the at least two components.

12. The non-transitory computer readable storage medium of claim 11, wherein the at least two components include a photo-electric component and a Compton component.

13. The non-transitory computer readable storage medium of claim 11, further containing instructions which, when executed by the computer, cause the computer to perform the act of reconstructing the agent-based component to generate agent-based volumetric image data.

14. The non-transitory computer readable storage medium of claim 13, where the agent-based volumetric image data provides a quantitative map for the agent.

15. The non-transitory computer readable storage medium of claim 11, where the agent-based volumetric image data is substantially free of beam hardening artifact.

\* \* \* \* \*